United States Patent [19]

Grega née Tóth et al.

[11] Patent Number: 4,620,871
[45] Date of Patent: Nov. 4, 1986

[54] COMPOSITION FOR INCREASING PLANT PRODUCTIVITY PROTEIN NITROGEN LEVEL AND ANION UPTAKE, POSSESSING KINETIN-SUPPLEMENTING, CYTOKININ-LIKE AND MEMBRANE ACTIVITIES

[75] Inventors: Erzsébet Grega née Tóth; Enikö Koppány; Tibor Bódi; József Nagy; Zsolt Dombay, all of Miskolc; Tibor Szarvas, Budapest; László Horváth, Budapest; Ildikó Szabó née Murányi, Budapest; József Márton, Budapest; Béla Pozsár, Jr., Budapest; Sándor Virányi, Budapest; Peter Simon, Budapest; József Keserü, Budapest; József Eifert, Budapest, all of Hungary

[73] Assignee: Eszakmagyarorszagivegyimuvek, Gyartelep, Hungary

[21] Appl. No.: 301,822

[22] Filed: Sep. 11, 1981

[30] Foreign Application Priority Data

Sep. 12, 1980 [HU] Hungary .............................. 2237/80

[51] Int. Cl.⁴ ...................... A01N 43/52; A01N 43/58
[52] U.S. Cl. .......................................... 71/92; 71/76; 71/77; 71/DIG. 1
[58] Field of Search ...................................... 71/92, 76

[56] References Cited

U.S. PATENT DOCUMENTS

| | | | |
|---|---|---|---|
| 2,614,916 | 10/1952 | Hoffmann et al. | 71/92 |
| 2,654,689 | 10/1953 | Ligett et al. | 424/250 |
| 2,940,844 | 6/1960 | Gysin et al. | 71/92 |
| 3,317,554 | 5/1967 | Goldsmith et al. | 71/92 |
| 3,592,822 | 7/1971 | Gilbert et al. | 71/92 |
| 3,736,121 | 5/1973 | Zeeh et al. | 71/92 |
| 4,229,204 | 10/1980 | Howe | 71/76 |

FOREIGN PATENT DOCUMENTS 2330319 7/1977 France ..................................... 71/92

OTHER PUBLICATIONS

Grzycka, "Preliminary Evaluation etc.," (1977), CA 89, No. 100876w, (1978).

*Primary Examiner*—Glennon H. Hollrah
*Attorney, Agent, or Firm*—Karl F. Ross; Herbert Dubno

[57] ABSTRACT

The invention relates to new compositions which contain 0.5 to 90% by weight of a phthalazine derivative having the general formula (I),

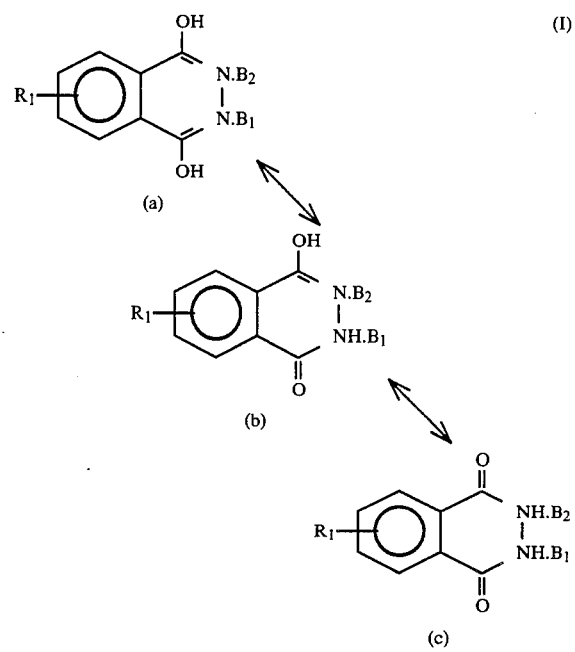

wherein
$R_1$ stands for hydrogen, halogen, a straight-chained or branched $C_{1-4}$ alkyl group having optionally a chlorine or hydroxy substituent, a $C_{2-4}$ alkenyl group, or an optionally alkyl-substituted amino, sulfhydryl or hydroxy group, and
$B_1$ and $B_2$, which may be identical or different, have no meaning or stand for guanidine and/or hydrazine base, and/or an imidazole derivative of the general formula (II),

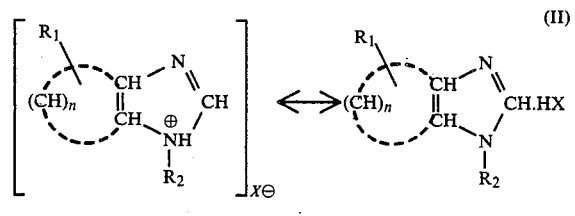

wherein
n is equal to zero or 4,
$R_2$ stands for hydrogen, a straight-chained or branched $C_{1-5}$ alkyl group having optionally a chlorine or hydroxy substituent, or a $C_{2-5}$ alkenyl group,
X stands for an organic or inorganic anion, and
in the compounds of the general formula (II) wherein n is equal to 4 $R_1$ has the same meanings as defined above, together with 10 to 95% by weight of one or more solid and/or liquid carrier(s) and 1 to 10% by weight of one or more surfactant(s).

The new compositions according to the invention increase the productivity, protein nitrogen level and anion uptake of plants, furthermore they also possess kinetin-supplementing, cytokinin-like and membrane activities. The new compositions can be applied to advantage for increasing crop yield and the nutrient value of the crop.

6 Claims, No Drawings

COMPOSITION FOR INCREASING PLANT PRODUCTIVITY PROTEIN NITROGEN LEVEL AND ANION UPTAKE, POSSESSING KINETIN-SUPPLEMENTING, CYTOKININ-LIKE AND MEMBRANE ACTIVITIES

The invention relates to new compositions for increasing plant productivity, protein nitrogen level and anion uptake, which also possess kinetin-supplementing, cytokinin-like and membrane activities.

The compositions according to the invention contain 0.5 to 90% by weight of a phthalazine derivative having the formula (I).

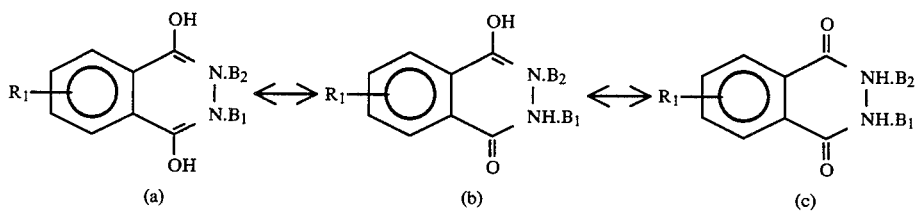

wherein
$R_1$ is hydrogen, halogen, a straight-chain or branched $C_{1-4}$ alkyl group having optionally a chlorine or hydroxy substituent, a $C_{2-4}$ alkenyl group, or an optionally alkyl-substituted amino, sulfhydryl or hydroxy group, and $B_1$ and $B_2$, which may be identical or different, have no meaning or stand for guanidine and/or hydrazine base, and/or an imidazole derivative of the formula (II),

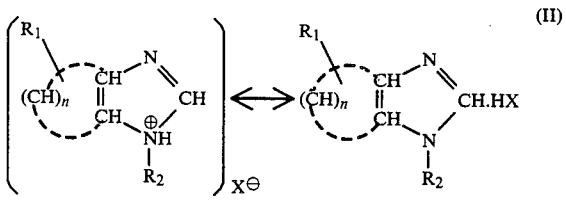

wherein
n is equal to zero or 4,
$R_2$ stands for hydrogen, a straight-chained or branched $C_{1-5}$ alkyl group having optionally a chlorine or hydroxy substituent, or a $C_{2-5}$ alkenyl group,
X stands for an organic or inorganic anion, preferably chloride or bromide ion, and
in the compounds of the formula (II) wherein n is equal to 4 $R_1$ has the same meanings as defined above, together with 10 to 95% by weight of one or more solid and/or liquid carrier(s) and 1 to 10% by weight of one or more surfactant(s).

Beside fertilizers and pesticides, chemicals which have been used for a long time in plant cultivation, the use of substances which influence the growth and crop yield of plants has become increasingly widespread in the last decades. These latter substances are generally referred to as regulators.

Most of the regulators are natural or synthetic hormones capable of influencing or regulating various processes of plant development [Kölcsei, M., Nádasy, M.: Magyar Kémikusok Lapja XXXIV, No. 3, pp. 122–126 (1979) (in Hungarian)].

The natural and synthetic auxines, which are indoleacetic acid derivatives, exert multiple influences on the vital processes of plants. The synthetic auxines can be classified into four main groups, i.e. indole derivatives, naphthyl derivatives, phenoxy derivatives and benzoic acid derivatives. The most widespread representatives of these substances are methyl naphthylacetate, which is applied as a dusting composition for inhibiting the sprouting of potato, and potassium naphthylacetate which is utilized to promote the rooting of cuttings and to inhibit premature fruit fall.

Gibberellines, which form a further main group of regulators, are capable of and utilized in practice for stimulating plant growth, inducing flowering and resolving the repose period.

Cytokinins, which form the third main group of regulators, influence the biological processes of plants from many sides. They promote cell division, retard senescence processes, suspend dominance and resolve the repose period. Of the natural cytokinins zeatin and lupin are known, they do not have, however, wide practical utilization.

The fourth main group of regulators encompasses the abscissins, which participate in the endogeneous regulation of senescence and also possess growth inhibiting and organ abscission promoting effects. Although more than 70 types of compounds with a xanthonine skeleton, possessing abscissic acid-like effects, have been synthetized so far, they have had no practical utilization.

Ethylene, a substance which forms in great amounts during the ripening process of fruits and accelerates the ripening process, is the only gaseous hormone. For the same purpose 2-chloroethylphosphonic acid is utilized in practice.

Beside plant hormones [auxines, gibberellines, cytokinins, plant growth retardants (PGR), abscissins, ethylene, etc.] various other compounds with biological activities have also been utilized in agrochemistry. Thus e.g. 2-chloroethyltrimethyl-ammonium chloride (CCC), a substance belonging to the PGR group, is widely used to increase the crop yield of wheat and barley (U.S. Pat. No. 3,156,544). The endogeneous cytokinins (zeatine, lupin) and the synthetic cytokinins (kinetin, benzyladenine, etc.) also increase significantly the crop and protein yield. The synthesis of these substances is, however, very expensive, which strongly inhibits their agrotechnical utilization [Skoog, F., Strong, F. M., Miller, C. O.: Science 148, pp. 532–533 (1965)].

The Hungarian patent specification No. 162,937 describes 2-chloroethane-(thiono)-phosphonic acid amide derivatives as substances for promoting germination, stimulating the development of shoots and accelerating ripening.

The Hungarian patent specification No. 163,510 discloses compositions containing thiourea derivatives, which promote the abscission of fruits. The Hungarian patent specification No. 164,190 teaches that certain haloethanesulfinic acids, such as 2-chloroethanesulfinic acid bromide, accelerate ripening, delay senescence and inhibit the growth of plants.

It is disclosed in the Hungarian patent specification No. 164,512 that if plant seeds are treated prior to sowing with a bis(dimethyl-ammonium)-p-chlorobenzyl phosphate derivative, the grain yield and nitrogen uptake increase.

The Hungarian patent specifications Nos. 164,587 and 164,866 disclose that β-haloethyl silanes, like ethylene, accelerate ripening.

According to the Hungarian patent specification No. 164,885 certain pyrimidine derivatives, such as 2-methylthio-4-ethylamino-5-nitro-6-methylamino-pyrimidine, and salts thereof possess germination inhibiting effects and also inhibit longitudinal cell growth.

The Hungarian patent specification No. 167,576 describes s-triazine-dione derivatives for influencing the flowering and gamogenesis of plants. Compositions containing allophane imidates, which also influence plant flowering and gamogenesis, are disclosed in the Hungarian patent specification No. 168,916.

According to the Hungarian patent specification No. 170,761 certain phthalimide derivatives, such as 3-trichloromethyl-phthalamide and 1-(3-chlorophthalimido)-cyclohexylcarboxamide, accelerate the emergence and growth of plants.

Compositions for increasing the sugar content of plants, containing 2-(aminoalkoxy)-4-phenyl-thiazole derivatives or 2,4-bis(N'-methyl-4'-pyridilium)-s-triazole diiodide, are described in the Hungarian patent specifications Nos. 162,520 and 165,576, respectively.

The Hungarian patent specification No. 165,576 describes compositions containing gibberelline plus an imidazole derivative, and fungicides plus certain herbicidal agents in very low concentrations, which accelerate the growth of sugar beet leaves. These compositions have not, however, been utilized in practice.

The endogeneous (zeatin, lupin) and synthetic (kinetin, benzyladenine, etc.) forms of cytokinins are all 6-amino-purine derivatives, the main biological effect of which is the acceleration of the mitosis frequency [Strong, F. M.: Topics in microbial chemistry, Wiley, New York (1958); Skoog, F., Strong, F. M., Miller, C. O.: Science 148, pp. 532-533 (1965)]. Beside this main effect, cytokinins proved to possess various other side effects as well, which can be utilized to advantage for plant cultivation, horticultural and microbiological purposes. Thus (a) they promote the fresh and dry weight gain of callus and mericlone cultures, (b) they lead to a more favorable accumulation of organic substances in the vegetative and generative organs, (c) they promote chlorophyll preservation and increase of its photochemical activity, (d) they promote the rejuvenation of leaf tissue, which results in the retardation of senescence, (e) they increase the intensity of the photosynthetic fixation of carbon dioxide, (f) they increase the photolytic activity which can be measured by the decomposition of HTO, (g) they increase the intensity of the amino acid and protein synthesis, particularly by increasing significantly the absolute and relative amounts of protein nitrogen fraction soluble in 0.5% sodium chloride solution, and (h) they increase the intensity of nucleic acid synthesis.

Up to now, however, only laboratory scale methods have been described for the synthesis of adenine base and specific derivatives thereof. Due to the high expenses of their production the promising effects mentioned above could not be utilized in plant cultivation, horticulture and microbiology. Thus, in spite of the fact that a vast number of compositions with PGR-effects were reported, no cytokinin-like composition was applied in the practice of agriculture, particularly not under large-scale conditions. The known compositions with PGR effects do not possess the characteristic main effect of cytokinins, thus they cannot exert cytokinin-like activity. This is the reason why no composition with cytokinin-like effects can be found on the market.

In our research work directed to increased plant growth, productivity, protein level and crop yield it has been found that the compositions according to the invention, which contain 0.5 to 90% by weight of a phthalazine derivative of the formula (I) and/or an imidazole derivative of the general formula (II), together with 10 to 95% by weight of one or more liquid and/or solid carrier(s) and 1 to 10% by weight of one or more surfactant(s), can be applied to advantage and with very favorable results in influencing certain plant physiological processes.

Where compositions including both a phthalazine derivative and an imidazole derivative are employed, it is preferred that said compositions contain 0.5 to 90% by weight of a 4:1-1:4 mixture of the phthalazine of the formula (I) and the imidazole of the formula (II), together with 10 to 90% by weight of one or more solid carriers, preferably amorphous silicic acid, or a ground mineral, and 1 to 15% by weight of one or more surfactants, preferably a mixture of an anionic and a nonionic tenzide.

A more preferred feature of the invention includes compositions containing 0.5 to 70% by weight of a 1:4-4:1 mixture of a phthalazine derivative of the formula (I) and an imidazole derivative of the formula (II), together with 30 to 80% by weight of one or more liquid diluents, preferably a nonphytotoxic oil, and 1 to 20% by weight of one or more solid carriers, preferably active silicic acid, and 1 to 15% by weight of one or more surfactants, preferably a mixture of an anionic and a nonionic tenzide.

Some phthalazine derivatives having the formula (I) have already been described in the literature [Curtius, Hoesch: J. prakt. Chem. 76, 2, 301 (1908); Draw. Hatt: J. Chem. Soc. 1, 16 (1937); Stanly, Parker: J. Am. Chem. Soc. 56, 241 (1934); Barber, Wrogg: J. Chem. Soc. 6, 1458 (1948)]. These references did not give, however, any information about the effects of these compounds exerted on protein level, photosynthesis and plant productivity.

It is known that 1,4-dihydroxyphthalazine occurs in three tautomeric forms; therefore the compounds of the formula (I) have been drawn in three different forms (a, b and c, respectively). The term "a compound of the formula (I)" encompasses all the possible isomers and isomeric mixtures of the respective phthalazine derivatives.

According to the U.S. Pat. No. 2,654,689 1,4-dihydroxyphthalazine and metal salts thereof possess fungicidal effects.

Some of the imidazole derivatives having the formula (II) have also been described in the literature [Auwers, Mauss: Chem. Ber. 61, 2414 (1928); Davies, Mamalis, Petrow, Sturgeon: J. Pharm. Pharmacol. 3, 420 (1951); Weidenhagen, Train, Wagner, Nordström: Chem. Ber. 75, 1936 (1942); Pozharsky, Simonov: Zh. Obsch. Khim. 33, 179 (1963)]. The effects of these compounds exerted on protein level, photosynthesis and plant productivity were, however, unknown till now.

It has been observed that the compositions according to the invention, which contain a phthalazine derivative of the formula (I) and/or an imidazole derivative of the formula (II) together with one or more liquid and/or solid carrier(s) or diluent(s) and surfactant(s), can be applied to influence favourably the physiological processes on a wide variety of cultivated plants, and exert their beneficial effects in relatively low concentrations (1 to 200 ppm or 0.5 kg of active agent/hectare).

It has also been observed that the compositions which contain phthalazine derivatives of the formula (I) exert more significant effects on plant productivity, protein synthesis and photosynthesis than the compositions described in the Hungarian patent specification No. 170,761, which latter contain as active agent phthalimide derivatives, i.e. compounds with closely related chemical structures. These known compositions exert just the opposite regulating effects, furthermore they influence only plant growth (more particularly, plant height), but do not act on the protein level and photosynthesis.

It has also been observed that the imidazole derivatives of the formula (II) which, unlike cytokinins, can be synthesized by inexpensive methods so that their agricultural utilization is economic, possess not only cytokinin-like cell-biological effects, but have membrane activity (i.e. promote the anion uptake), as well, which does not appear to be the case with the endogeneous and synthetic cytokinins.

It has also been observed, surprisingly, that while the new compositions increase the organic substance production almost aspecifically on almost all of the plant varieties examined, the extent of protein synthesis- and photosynthesis-stimulating effect already depends on the type of the plant treated.

We have also elaborated and applied well-reproducible methods to examine the biological effects of the compositions according to the invention and to test how they influence the various vital processes of plants. The effects exerted on protein synthesis were examined by isotope technique, measuring the incorporation of labelled amino acids [glycine-1-$^{14}$C, glycine-2-$^{14}$C and methionine-(S-methyl-$^{14}$C), respectively]. The promotion of photosynthesis was also examined by isotope technique, measuring the incorporation of labelled carbon dioxide ($^{14}CO_2$). The effects exerted on nutrient uptake were tested by measuring the incorporation of labelled phosphate ions, whereas the inhibiting effect exerted on the decomposition of chlorophyll was tested by measuring the extinction of the methanol extracts as 665 m$\mu$.

The results of the laboratory tests were in complete agreement with the results observed when treating the plants under field conditions.

Based on the test results, the compositions of the invention exert the following effects on the vital processes of plants:

(a) the internodium development shortens, e.g. for vines, the number and dry weight of leaves increases, and the carbon/nitrogen ratio decreases favorably;

(b) owing to the promotion of root development (root factor) the growth of overground (aerial) shoots becomes more intense, whereupon the period of vegetative development shortens (e.g. by 6 weeks for brewer's barley) and the development of generative organs increases, which involves the increase of crop yield;

(c) in perennial papilionaceae (e.g. in alfalfa cultures) and in pasturage cultures (e.g. maize for silage, grass) the uptake of soil nitrogen and phosphorous increases, thus the protein nitrogen content of the leaves increases considerably and the carbon/nitrogen ratio decreases;

(d) when soybean, maize, brewer's barley, wheat, etc. are treated with a composition according to the invention, the total nitrogen content of the grain crop increases by about 20%, coupled with an even higher increase in protein nitrogen content;

(e) when sugar beet is treated with a composition according to the invention, the crop yield and the polarimetrically measurable sugar content increase, which involve an increase in sugar yield attainable on unit area; furthermore the plants reach their genetically determined maximum sugar content within a shorter period, thus they can be harvested earlier;

(f) when vines are treated with a composition according to the invention prior to flowering and then twice more until ripening, the average weight of the clusters, the thousand-berry weight and the sugar content determined by refractometry increase;

(g) treatments with a composition according to the invention considerably accelerate the rooting of vine and fruit-tree graft, the differentiation of stock and sprouts and ripening, which also have a favorable influence on the maturation and frost resistance of the stock;

(h) owing to the fact that the compositions according to the invention increase the frequency of mitosis, they can be applied to advantage in plant tissue cultivation to effect tissue and organ differentiation of the callus;

(i) the phytotoxic effects exerted on cultivated plants by various herbicides can be counterbalanced or corrected, when the plants are sprayed with a composition according to the invention in order to avoid their damaging.

The cultivated plants can be treated with the compositions according to the invention prior to sowing or planting, or treatment can be performed after sowing or planting by spraying the composition onto the soil. The plants can also be treated with the compositions according to the invention at one or more pre-determined stage of their development. The timing of treatment depends on the development stage and property of the plant to be influenced. In the majority of the cases appropriate influencing effects can be achieved even upon a single treatment, in some instances, however, multiple treatments are preferred (e.g. on vines).

The dose of the treatment varies, depending on the actual composition of the preparation, generally between 0.5 and 20 kg/ha; in most instances, however, even a very low dose (e.g. 0.5 to 2 kg/ha) is sufficient to attain the desired result. The preparations according to the invention do not exert any phytotoxic effect on cultivated plants even when applied in very high dose (e.g. 20 to 30 kg/ha). As a further advantage, the compositions according to the invention are completely free to skin irritating, skin sensitizing (allergenic) and eye irritating effects, and they are practically non-toxic ($LD_{50}$: 2500 mg/kg).

The use of the compositions according to the invention in various fields of agriculture (plant cultivation) is described in detail in the examples.

The phthalazine derivatives of the formula (I) can be prepared in a manner known per se in that the appropriately substituted phthalic acid or a reactive derivative thereof (e.g. its anhydride, chloride, ester, etc.) is reacted with an excess of hydrazine or hydrazine sulfate at 90° to 160° C. in a solvent medium. As a general rule, the increase of the hydrazine excess, the temperature and the reaction time favor the formation of the dihydroxyphthalazine compound. Depending on the reaction conditions, a monohydrazide derivative of the formula (III),

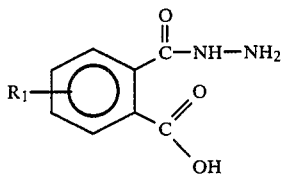

a dihydrazide derivative of the formula (IV),

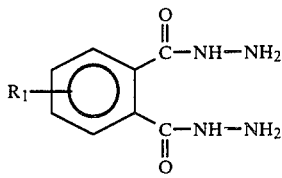

an N-aminophthalimide of the formula (V),

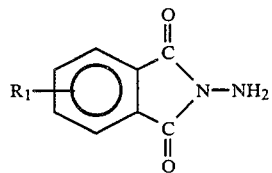

and/or a mixed amide-hydrazide compound of the formula (VI)

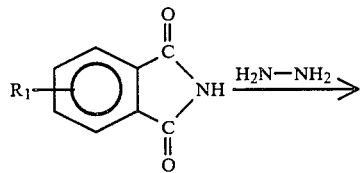

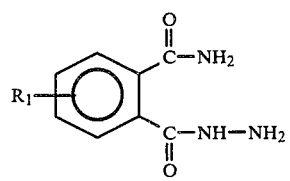

can be formed. The resulting mono-and dihydrazides, as well as the mixed amide-hydrazide compound undergo ring closure upon heating to form a dihydroxyphthalazine.

The resulting dihydroxyphthalazine derivative can be reacted then with hydrazine or guanidine base in a solvent medium to obtain a salt-like compound. The resulting substance is separated by filtration, washed and dried.

The imidazolium derivatives of the formula (II) can be prepared in a manner known per se in that the appropriately substituted imidazole is reacted with an alkyl halide or alkyl chloroformate at 50° to 160° C. in an organic solvent medium (e.g. acetone, benzene, toluene, etc). The resulting substituted imidazolium salt is separated by filtration, washed and dried. Depending on the reaction conditions, the resulting product may contain a minor amount of the respective dialkylated derivative as impurity. The amount of this dialkylated substance is, however, so small that it does not influence the effect of the composition.

If a pure product, free of dialkylated by-products, is to be obtained, the reaction is performed in two separate steps, i.e. the N-alkyl-imidazole is prepared first, and then it is converted into the respective imidazolium salt (e.g. halide, sulfate, etc.) in a separate step.

The preparation of the active agents [phthalazine derivatives of the formula (I) and imidazolium derivatives of the formula (II)] is described in the following Examples.

EXAMPLE 1

148.2 g (1 mole) of phthalic acid anhydride and 130 g (1 mole) of hydrazine sulfate are introduced into a 1500 ml flask equipped with a thermometer, a stirrer and a reflux condenser. Thereafter a solution of 90 g of sodium hydroxide in 800 ml of water is added to the mixture at 40° C., and the mixture is heated to boiling under constant stirring. The mixture is refluxed for one hour, thereafter it is cooled to 60° C., and its pH is adjusted to 5 to 6 with 50 ml of concentrated hydrochloric acid. The resulting mixture is stirred at 20° to 40° C. for 4 hours. The spearated solids are filtered off and dried at 80° to 100° C.

448 g (4 moles) of guanidine nitrate are introduced into a 2500 ml flask, the salt is suspended in 800 ml of ethanol, and then a solution of 224 g (4 moles) of potassium hydroxide in 500 ml of ethanol is added. After 0.5 hours of stirring the solution is filtered, and the filtrate is added to the solid dihydroxyphthalazine obtained in the first step. The resulting mixture is stirred at room temperature for one hour, then the separated white, crystalline substance is filtered off, washed and dried at 60° C.

219.4 g (0.86 moles, 86.3%) of dihydroxyphthalazine diguanidine salt are obtained. The white, microcrystalline substance melts at 280° C.

EXAMPLE 2

118.2 g (1 mole) of benzimidazole are introduced into 2000 ml flask equipped with a thermometer, a stirrer, a reflux condenser and a dropping funnel, and the solid is dissolved in 800 ml of toluene. 200 ml of isopropyl chloroformate are added to the stirred solution, under maintaining the temperature of the mixture at 20° C. When the addition is complete, the mixture is warmed to 60° C. and stirred for 2 hours at this temperature. The mixture is stirred then at 90° to 100° C. for additional two hours, finally it is cooled to 15° to 20° C. The separated greyish-white crystalline substance is filtered off, washed and dried at 80° C. 125.5 g (81.7%) of a substance melting at 134°–136° C. are obtained.

Similarly other phthalazine derivatives of the formula (I) and the other alkylimidazole derivatives of the formula (II) can be prepared.

The compositions according to the invention can be prepared as described in the following Examples.

EXAMPLE 3

65 g of 1,4-dihydroxyphthalazine diguanidine salt (technical quality; purity grade: 92%), 5 g of Ultrasyl VN-3 (filling agent), 20 g of Emulsogen M (emulsifying agent) and 111 g of vaseline oil (technical quality) are introduced into a laboratory ball mill. 400 g of glass beads, 1.5 mm in diameter, are added, and the mixture is milled for 1.5 hours at a rate of 775 r.p.m. The glass beads are separated from the mixture by sieving through a metal sieve with a gap size of 1 mm.

The resulting oily composition, containing 30% by weight of 1,4-dihydroxyphthalazine diguanidine salt, is emulsified in water to form a 1 w/w % emulsion. This emulsion is stable and free from sediments after 12 hours of standing. After 24 hours of standing a sediment separates from the emulsion, which can be emulsified reversibly upon gentle shaking.

EXAMPLE 4

48 g of N-isopropyl-benzimidazolium chloride (technical quality; purity grade: 94%), 4 g of Ultrasyl VN-3 (filling agent), 20 g Emulsogen M (emulsifying agent) and 128 g of vaseline oil (technical quality) are introduced into a laboratory ball mill. 400 g of glass beads, 1.5 mm in diameter, are added, and the mixture is milled for one hour at a rate of 775 r.p.m. The glass beads are separated from the mixture by sieving through a sieve with a gap size of 1 mm.

The resulting oily composition, containing 20% by weight of N-isopropyl-benzimidazolium chloride, is diluted with water to an active agent content of 1% by weight. This emulsion is stable and free from sediments after standing for 12 hours.

EXAMPLE 5

22 g of 1,4-dihydroxyphthalazine diguanidine salt (technical quality; purity grade: 92%), 4 g of Ultrasyl VN-3 (filling agent), 20 g of Emulsogen M (emulsifying agent) and 117 g of vaseline oil (technical quality) are introduced into a laboratory ball mill. 400 g of glass beads, 1.5 mm in diameter, are added, and the mixture is milled for 2 hours at a rate of 775 r.p.m. The glass beads are separated from the mixture by sieving through a sieve with a gap size of 1 mm. The resulting oily composition, containing 10% by weight of 1,4-dihydroxyphthalazine diguanidine salt, is diluted with water to an active agent content of 1% by weight. This emulsion is stable and free from sediments after standing for 12 hours.

EXAMPLE 6

22 g of 1,4-dihydroxyphthalazine diguanidine salt (technical quality; purity grade: 92%), 20 g of N-isopropylbenzimidazolium chloride (technical quality; purity grade: 96%). 4 g of Ultrasyl VN-3 (filling agent), 20 g of Emulsogen M (emulsifying agent) and 134 g of vaseline oil (technical quality) are introduced into a laboratory ball mill. 400 g of glass beads, 1.5 mm in diameter, are added, and the mixture is milled for 2.5 hours at a rate of 775 r.p.m. The glass beads are separated from the mixture by sieving through metal sieve with a gap size of 1 mm.

The resulting oily composition is diluted to twentyfold volume with water to obtain an emulsion stable for 12 hours.

EXAMPLE 17

11 g of N-isopropyl-benzimidazolium chloride (technical quality; purity grade: 96%), 4 g of Ultrasyl VN-3 (filling agent), 16 g of Emulsogen M (emulsifying agent) and 170 g of vaseline oil (technical quality) are introduced into a laboratory ball mill. 400 g of glass beads, 1.5 mm in diameter, are added, and the mixture is milled for one hour at a rate of 775 r.p.m. The glass beads are separated from the mixture by sieving through a metal sieve with a gap size of 1 mm.

The resulting composition is diluted to tenfold volume with water to obtain an emulsion stable for 12 hours.

EXAMPLE 8

52 g of 1,4-dihydroxyphthalazine diguanidine salt, g of Zeolex-444 (solid carrier), 6 g of powdery sulfite waste liquor, 3 g of Supermittel-1494 (dispersing agent), 1 g of Netzer IS (Wetting agent) and 0.2 g of Tensia defoamer (antifoaming agent) are introduced into a laboratory powder mixer. The mixture is homogenized, and then milled on an "Alpine 100 LU" type laboratory ultraplex mill.

The resulting composition, containing 50% of active agent, is diluted with water to form a 0.5% suspension. The floatability of the solids is 84–87% after 0.5 hours of standing, the wet sieve residue (examined on a DIN 100 sieve) is 1–1.5%.

EXAMPLE 9

91 g of technical 1,4-dihydroxyphthalazine diguanidine salt, 4 g of talc, 4 g of powdery sulfite waste liquor, 1 g of Netzer IS (wetting agent) and 0.2 g of methylene blue (dyestuff) are introduced into a laboratory powder mixer. The mixture is homogenized, and then milled on an Alpine 100 LU type laboratory ultraplex mill.

The wet sieve residue of the composition (examined on a DIN 100 sieve) is 3–4%.

EXAMPLE 10

53 g of N-isopropyl-benzimidazolium chloride, 37 g of Zeolex-444 (solid carrier), 5 g of powdery sulfite waste liquor, 3.5 g of Supermittel-1494 (dispersing agent), 1.5 g of Netzer IS (wetting agent) and 0.3 g of Tensia defoamer (antifoaming agent) are introduced into a laboratory powder mixer. The mixture is homogenized and then milled on an Alpine 100 LU type laboratory ultraplex mill.

The resulting composition, containing 50% of active agent, is diluted with water to form a 0.5% suspension. The floatability of the solids is 86–90% after 0.5 hours of standing; the wet sieve residue (examined on a DIN 100 sieve) is 0.5–1.5%.

EXAMPLE 11

84.2 g of N-isopropyl-benzimidazolium chloride, 9.5 g of talc, 5 g of powdery sulfite waste liquor, 1 g of Netzer IS (wetting agent) and 0.3 g of methylene blue (dyestuff) are introduced into a laboratory powder mixer. The mixture is homogenized and then milled on an Alpine 100 LU type laboratory ultraplex mill.

The wet sieve residue of the resulting composition (examined on a DIN 100 sieve) is 2-4%.

EXAMPLE 12

44.5 g of technical 1,4-dihydroxyphthalazine diguanidine salt, 42 g of N-isopropyl-benzimidazolium chloride, 9.5 g of talc, 5 g of powdery sulfate waste liquor, 1 g of Netzer IS (wetting agent) and 0.4 g of methylene blue (dyestuff) are introduced into a laboratory powder mixer. The mixture is homogenized, and then milled on an Alpine 100 LU type laboratory ultraplex mill. The wet sieve residue of the resulting composition (examined on a DIN 100 sieve) is 3-5%.

The plant growth regulating compositions according to the invention can be presented as a solid formulations (powder mixtures, granulates, etc.). In this instance e.g. kaolin, bentonite, active silicic acid, gypsum, calcium carbonate or talc can be applied as solid carrier or filling agent.

The compositions can also be presented as liquid formulations, of which the oily formulations are the most preferred, since they can be sprayed out easily at any stage of the development of the plant. Of the liquid diluents usable to produce oily formulations e.g. vaseline oil, fruit tree oils, other vegetable oils and non-phytotoxic mineral oil derivatives are to be mentioned.

Both the solid and the liquid formulations must contain surfactants, which may be cationic, anionic and nonionic tenzides and mixtures thereof. As cationic tenzides e.g. quaternary ammonium compounds (such as cetyl-trimethylammonium chloride), as anionic tenzides e.g. salts of dodecyl-benzenesulfonic acid, whereas as nonionic tenzides e.g. polyoxyethylene-alkylphenols, polyoxyethylene-sorbitanes, polyoxyethylene-triglycerides etc. can be applied. The anionic and nonionic tensides can also be utilized as mixtures.

The plant biological effects of the compositions according to the invention, as well as their use in plant cultivation are demonstrated by the following non-limiting Examples.

EXAMPLE 13

Effect on the daily growth of tobacco callus

The compositions according to the invention were diluted with water to an active agent content of 10 ppm, and then were added to the culture media prior to incubation. An untreated culture medium served as control. Tobacco callus was grown on the treated and untreated culture media (incubation period: 3 weeks), and the daily growth, the increase in cell number and the frequency of mitosis were measured according to the method of Skoog. The results of the test are summarized in Table 1.

TABLE 1

| Test No. | Treatment | Daily growth, mg | Cell number/ g. $10^4$ units | Frequency of mitosis % |
|---|---|---|---|---|
| 1 | Untreated control | 16.0 | 227.7 | 100 |
| 2 | 1,4-Dihydroxyphthalazine diguanidine salt | 19.3 | 266.0 | 117 |
| 3 | N—(n-Propyl)-benzimidazolium bromide | 22.8 | 327.5 | 143 |
| 4 | 1:1 mixture of the active agents used in Tests 2 and 3 | 24.1 | 375.2 | 165 |

The date demonstrate clearly that the treatment with the composition according to the invention resulted in an increase of the daily growth and cell number. The frequency of mitosis increased by 17-65%.

EXAMPLE 14

Effect on the growth of tobacco callus

The test described in Example 13 was repeated so that a culture medium containing 1 ppm of kinetin was used as control, and the compositions according to the invention were applied in amounts corresponding to 2 ppm of active agent. The results are listed in Table 2.

TABLE 2

| Test No. | Treatment | Dry weight of the callus mg | Speed of growth Index | % |
|---|---|---|---|---|
| 1 | Kinetin | 174.11 | 97.17 | 100 |
| 2 | 1,4-Dihydroxyphthalazine diguanidine salt | 170.92 | 98.23 | 98.16 |
| 3 | N—(n-Propyl)-benzimidazolium chloride | 194.09 | 116.89 | 119.0 |
| 4 | 1:1 mixture of the active agents used in Tests 2 and 3 | 198.21 | 119.37 | 121.52 |

EXAMPLE 15

Effect on the growth of callus isolated from *Datura innoxia* Mill. roots

The tests described in Examples 13 and 14 were repeated so that a culture medium containing 2 ppm of kinetin was used as control. The results are summarized in Table 3.

TABLE 3

| Test No. | Treatment | Fresh weight of the callus g | Dry weight of the callus mg | Dry substance % | Growth Fresh weight | Growth Dry weight | Speed of growth mg/day |
|---|---|---|---|---|---|---|---|
| 1 | Control with kinetin | 4.9694 | 175.06 | 3.52 | 15.56 | 15.56 | 98.28 |
| 2 | 1,4-Dihydroxyphthalazine diguanidine salt | 7.6110 | 269.07 | 3.53 | 24.37 | 24.46 | 149.20 |
| 3 | N—(n-Propyl)-benzimidazolium bromide | 6.5772 | 209.13 | 3.17 | 20.92 | 18.78 | 128.10 |
| 4 | Control without kinetin | 0.3968 | 28.08 | 7.07 | 0.32 | 1.65 | 1.97 |
| 5 | 1,4-Dihydroxyphthalazine diguanidine | 0.9258 | 66.11 | 7.14 | 2.08 | 5.25 | 12.77 |

TABLE 3-continued

| Test No. | Treatment | Fresh weight of the callus g | Dry weight of the callus mg | Dry substance % | Growth Fresh weight | Growth Dry weight | Speed of growth mg/day |
|---|---|---|---|---|---|---|---|
| 6 | salt N—(n-Propyl)-benzimidazolium bromide | 0.6120 | 43.29 | 7.07 | 1.04 | 3.09 | 6.36 |

The percentage growth promoting effects of the compositions according to the invention, determined in the presence and in the absence of kinetin, are listed in Table 4.

TABLE 4

| No. | Treatment | With kinetin | Without kinetin |
|---|---|---|---|
| 1 | Control | 100 | 100 |
| 2 | 1,4-Dihydroxyphthalazine diguanidine salt | 156 | 648 |
| 3 | N—(n-Propyl)-benzimidazolium bromide | 134 | 322 |

EXAMPLE 16

Inhibition of the decomposition of chlorophyll in barley, soybean, bean, alfalfa and maize The active agent to be tested was dissolved in distilled water to form a 200 ppm solution, and leaf segments of the plants under examination, weighing 200 mg, were floated on the surface of the solution for 4 days in the dark. Thereafter chlorphyll was extracted from the leaf segments with methanol.

To determine the starting state, chlorophyll was extracted with methanol from untreated leaf segments weighing 200 mg. In the control test the leaf segments, weighing 200 mg, were floated on the surface of distilled water for 4 days in the dark, and then chlorophyll was extracted from the leaf segments with methanol.

The chlorophyll concentration was determined by measuring the extinction of the extracts at 665 m$\mu$. The results are summarized in Tables 5 and 6.

TABLE 5

| Test No. | Plant | Untreated controls | Treatments 1,4-Dihydroxy-phthalazine Chlorophyll, mg | Treatments Diguanidine salt Chlorophyll, mg | Promotion, % |
|---|---|---|---|---|---|
| 1 | Barley | 3.7 | — | 9.7 | 162 |
| 2 | Soybean | 3.5 | 4.2 | — | 20 |
| 3 | Soybean | 3.5 | — | 5.4 | 54 |
| 4 | Bean | 4.2 | 5.8 | — | 38 |
| 5 | Bean | 4.2 | — | 6.5 | 54 |

TABLE 6

| | N—Alkyl-benzimidazolium bromide of the general formula (II) used in the treatment | Alfalfa Chlorophyll content mg | Alfalfa Promotion % | Maize Chlorophyll content mg | Maize Promotion % |
|---|---|---|---|---|---|
| 1 | N—methyl compound | 0.83 | 6.4 | 0.80 | 23.0 |
| 2 | N—ethyl compound | 0.85 | 8.9 | 0.79 | 21.5 |
| 3 | N—bromoethyl compound | 0.64 | — | 0.71 | 9.2 |
| 4 | N—(n-propyl) compound | 0.96 | 23.0 | 0.82 | 26.1 |
| 5 | N—(n-butyl) compound | 0.81 | 3.8 | 0.76 | 16.9 |
| 6 | Untreated control | 0.78 | — | 0.65 | — |

For alfalfa and maize the chlorphyll contents of 100 mg of green plant were examined.

The test results demonstrate clearly that the compositions according to the invention effectively inhibit the decomposition of chlorophyll.

EXAMPLE 17

Effect on the preservation of chlorophyll

The effects of cytokinin-like regulators on the preservation of chlorophyll are summarized in Table 7. Endogeneous and synthetic cytokinins were applied as comparative substances. Solutions with varying concentrations, but always more dilute than $10^{-4}$ moles, were applied in the tests. The results indicate that all of the cytokinin-like regulators promote chlorphyll in a concentration of 200 ppm, the extent of promotion is, however, somewhat lower than that observed with the endogenous and synthetic cytokinins. The radiobiological test results indicate that the cytokinin-like regulators do not exert any phytotoxic effect even when applied in a concentration of 10.000 ppm.

The tests were performed on Pinto beans. The plants were treated with an endogenous cytokinin (zeatine), synthetic cytokinins (kinetin, benzyladenine) or cytokinin-like compounds, respectively, and the chlorophyll content of the leaves was determined 2 weeks after the treatment by measuring the extinction of the extract of the leaves at 665 m$\mu$. The results, related to 200 mg fresh weight, are listed in Table 7.

TABLE 7

| Test No. | Treatment | ppm | Extinction | Promotion % |
|---|---|---|---|---|
| 1 | Untreated control | — | 0.671 | — |
| 2 | Zeatin | 20 | 1.283 | 91.3 |
| 3 | Kinetin | 30 | 1.120 | 66.0 |
| 4 | Benzyladenine | 30 | 1.229 | 83.1 |
| 5 | 1,4-Dihydroxyphthalazine diguanidine salt | 200 | 0.985 | 46.8 |
| 6 | N—(n-Propyl)-benzimidazolium bromide | 200 | 1.081 | 61.2 |

EXAMPLE 18

Stimulation of the protein level of soybean

The active agent to be tested was dissolved in distilled water to form a 200 ppm solution, and soybean leaf segments, weighing 200 mg, were floated on the surface of the solution for 24 hours. In the control test leaf segments, weighing 200 mg, were floated on the surface of distilled water.

The leaf segments were washed with distilled water, and then treated for 3 hours with 20 ml of a solution containing labelled amino acid (glycine-$^{14}$C; activity: 2 $\mu$Ci). After this exposition period the leaf segments were washed with an aboundant amount of water, and the protein content of the leaf segments was isolated in a manner known per se. Stock solution was prepared from the isolated protein, and the specific radioactivity of the solution was determined by liquid scintillation. The results are listed in Table 8.

TABLE 8

| Test No. | Treatment | Radioactivity mu Ci/100 mg | Stimulation, % |
|---|---|---|---|
| 1 | Untreated control | 11.9 | — |
| 2 | 1,4-Dihydroxyphthalazine | 16.1 | 35.3 |
| 3 | 1,4-Dihydroxyphthalazine diguanidine salt | 15.5 | 30.2 |
| 4 | N—(n-Propyl)-benzimidazolium bromide | 13.7 | 15.2 |
| 5 | 1:1 mixture of the active agents used in Tests 3 and 4 | 19.6 | 64.7 |

It appears from the data of Table 8 that, as a result of the treatments with the compositions according to the invention, the protein incorporation into soybean leaves increased by 15 to 65%.

EXAMPLE 19

Effects on protein synthesis

The stimulating effects of the compositions according to the invention exerted on protein synthesis, compared to the effects of cytokinins, are shown in Table 9. The data of Table 9 indicate that although the compositions according to the invention are less effective than the cytokinins examined, they still exert considerable stimulating effects with a tendency analogous to that of the cytokinins.

The tests were performed on leaves of Pinto bean. The leaf segments were treated with an endogeneous cytokinin (zeatin), synthetic cytokinins (kinetin, benzyladenine) or with the compositions according to the invention, respectively, by floating the leaf segments on the solution of the test substance for 18 hours. Thereafter the leaf segments were exposed to a labelled amino acid (glycine-2-$^{14}$C) for 3 hours, and the incorporation of the amino acid was determined by radiometry. The radioactivity data, expressed in units of 1000 dpm/200 mg fresh weight, are listed in Table 9.

TABLE 9

| Test | Treatment | ppm | Radioactivity of the TCA-insoluble fraction 1000 dpm/200 mg fresh weight | Stimulation, % |
|---|---|---|---|---|
| 1 | Untreated control | — | 3.17 | — |
| 2 | Zeatin | 20 | 6.18 | 95.1 |
| 3 | Kinetin | 30 | 5.36 | 69.4 |
| 4 | Benzyladenine | 30 | 5.92 | 87.0 |
| 5 | 1,4-Dihydroxy-phthalazine diguanidine salt | 200 | 4.40 | 39.0 |
| 6 | N—(n-Propyl)-benzimidazolium bromide | 200 | 4.52 | 42.7 |

EXAMPLE 20

Stimulation of the photosynthesis of plants

The compositions according to the invention were diluted with distilled water to an active agent content of 200 ppm, and leaf discs of alfalfa, soybean, bean and maize, weighing 200 mg each, were floated on the surfaces of the resulting solutions for 2 hours. Thereafter the treated leaf discs were place into the assimilation chamber of an appropriate measuring apparatus, and a known amount of radioactive carbon dioxide gas ($^{14}CO_2$) was introduced into the assimilation chamber from a reservoir by means of a gas feeder for 0.5 hours under carefully controlled illumination conditions. Thereafter the leaf discs were frozen with liquid nitrogen, triturated with 50% by weight perchloric acid in a potter homogenizer, and stock solutions were prepared from the resulting mixtures. The specific radioactivities of the stock solutions were determined by liquid scintillation.

In the control test untreated leaf discs were exposed to labelled carbon, dioxide, and the amount of carbon dioxide incorporated under such conditions was regarded as standard.

The percentage increase in the amount of incorporated labelled carbon dioxide, related to the standard, is given in Table 10.

TABLE 10

| | | Stimulation, % | | | |
|---|---|---|---|---|---|
| Test No. | Treatment | Alfalfa | Soybean | Bean | Maize |
| 1 | N—methyl-benzimidazolium bromide | — | — | 125 | — |
| 2 | N—ethyl-benzimidazolium bromide | — | — | 184 | — |
| 3 | N—bromoethyl-benzimidazolium bromide | — | — | 57 | — |
| 4 | N—(n-propyl)-benzimidazolium bromide | 12 | 236 | — | 84 |
| 5 | N—(n-butyl)-benzimidazolium bromide | — | — | 41 | 47 |
| 6 | 1,4-Dihydroxyphthalazine diguanidine salt | — | 67 | 4 | 12 |
| 7 | 1:1 mixture of the active agents used in Tests 4 and 6 | — | — | 41 | 47 |

It appears from the data of Table 10 that all of the compositions according to the invention stimulate the carbon dioxide incorporation of plants. The actual value of stimulation varies within wide limits, but the degree of stimulation is significant in most of the cases examined.

EXAMPLE 21

Stimulation of carbon dioxide fixation

The stimulating effects of the compositions according to the invention exerted on the photosynthetic fixation of carbon dioxide, compared to the effects of endogeneous and synthetic cytokinins, are demonstrated in Table 11. The data of Table 11 indicate that zeatin ("root factor") is the most potent stimulating agent, the effects of synthetic cytokinins approach to that of zeatin, and the cytokinin-like regulators are somewhat less potent than the synthetic cytokinins.

The tests were performed on leaves of Pinto beans. The leaf segments were treated with an endogeneous cytokinin (zeatin), synthetic cytokinins (kinetin, benzyladenine) or with the compositions according to the invention, respectively, by floating the leaf segments on the solution of the test substance for 18 hours, thereafter the leaf segments were exposed to labelled carbon dioxide (activity: 100 μCi/5000 ml of $^{14}CO_2$) for 0.5 hours. The radioactivity data, expressed in units of dpm/200 mg fresh weight, are listed in Table 11.

TABLE 11

| Test No. | Treatment | ppm | Radioactivity, dpm/ 200 mg fresh weight A | B | C | Stimulation, % |
|---|---|---|---|---|---|---|
| 1 | Untreated control | — | 2.14 | 0.18 | 2.32 | — |
| 2 | Zeatin | 20 | 5.12 | 0.46 | 5.58 | 140.8 |
| 3 | Kinetin | 30 | 4.15 | 0.37 | 4.52 | 95.2 |
| 4 | Benzyladenine | 30 | 4.87 | 0.41 | 5.28 | 128.0 |
| 5 | 1,4-Dihydroxy-phthalazine diguanidine salt | 200 | 3.38 | 0.31 | 3.69 | 59.3 |
| 6 | 1,4-Dihydroxy-phthalazine monoguanidine salt | 200 | 3.75 | 0.28 | 3.47 | 50.7 |
| 7 | N—(n-Propyl)-benzimidazolium bromide | 200 | 3.92 | 0.34 | 4.26 | 84.0 |

A = in the light
B = in the dark
C = photosynthetic

EXAMPLE 22

Stimulation of plant photolysis

The compositions according to the invention were diluted with distilled water to an active agent content of 500 ppm, and green parts of maize, weighing 200 mg, were treated with the resulting solutions for 2 hours. Thereafter the treated green plant parts were treated for one hour with 10 µCi/50 ml HTO, then the plant parts were frozen with liquid nitorgen, triturated, subjected to chromatographic separation, and the radioactivity of the isolated glycerol aldehyde was determined. The results, related to 1 mg dry weight, are listed in Table 12.

In the control test the green parts of maize were treated with distilled water only.

TABLE 12

| Test No. | Treatment | Radioactivity dpm/mg dry weight | Stimulation, % |
|---|---|---|---|
| 1 | N—(n-Propyl)-benzimidazolium bromide | 8.76 | 88 |
| 2 | 1,4-Dihydroxyphthalazine diguanidine salt | 11.42 | 146 |
| 3 | Untreated control | 4.64 | — |

The data listed in Table 12 indicate that the compositions according to the invention effectively stimulated the photolysis of plants.

EXAMPLE 23

Stimulation of photolytic activity

The stimulating effects of an endogeneous cytokinin (zeatin), synthetic cytokinins (kinetin, benzyladenine) and the cytokinin-like regulators according to the invention exerted on the photolytic activity connected to the decomposition of HTO were examined on leaves of Pinto bean. The leaf discs were floated for 18 hours on solutions of the substances under examination, and then exposed to a radioactivity of 200 µCi/100 ml for one hour to effect photolysis of HTO. The radioactivity data, expressed in units of dpm/mg of glucose, are given in Table 13.

TABLE 13

| Test No. | Treatment | ppm | Photolytic activity dpm/mg of glucose | Stimulation % |
|---|---|---|---|---|
| 1 | Untreated control | — | 7.64 | — |
| 2 | Zeatin | 20 | 15.94 | 108 |
| 3 | Kinetin | 30 | 13.96 | 82 |
| 4 | Benzyladenine | 30 | 17.21 | 125 |
| 5 | 1,4-Dihydroxy-phthalazine diguanidine salt | 200 | 13.72 | 79 |
| 6 | N—(n-Propyl)-benzimidazolium bromide | 200 | 14.08 | 84 |

EXAMPLE 24

Stimulation of nutrient uptake

The compositions according to the invention were diluted with distilled water to an active agent concentration of 200 ppm, and leaf segments of wheat, maize and pea, weighing 200 mg each, were treated with the solutions. Thereafter the treated green leaf segments were treated for 0.5 hours with a solution of labelled phosphate ions (radioactivity: 30 µCi/50 ml). After this exposition period the treated leaf segments and the untreated controls were processed in a manner known per se to isolate the nucleic acid fractions, and the isolated nucleic acid fractions were dissolved in 6 n ammonium hydroxide solution. Stock solutions were prepared from the resulting solutions, and the amount of labelled phosphate ions present in the stock solutions were measured by liquid scintillation. The results are summarized in Table 14.

TABLE 14

| Test No. | Plant | Control 1000 cpm/g | 1,4-Dihydroxyphthalazine diguanidine salt 1000 cpm/g | Stimulation, % | N—(n-Propyl)-benzimidazolium bromide 1000 cpm/g | Stimulation, % |
|---|---|---|---|---|---|---|
| 1 | Wheat | 17.4 | 29.3 | 68.5 | 22.8 | 31.0 |
| 2 | Maize | 31.2 | 47.0 | 50.6 | 39.3 | 25.9 |
| 3 | Pea | 23.3 | 38.4 | 51.7 | 32.7 | 29.2 |

It appears from the results that the incorporation of labelled phosphate ions into the nucleic acid fraction increased by 26–70% upon treating the plants with the compositions according to the invention, i.e. the nutrient uptake of the plants increased.

EXAMPLE 25

Stimulation of membrane activity

Unlike endogeneous and synthetic cytokinins, the compositions according to the invention also possess membrane-active side effects. The stimulation of nitrate uptake provoked by the compositions according to the invention, which manifests in the increase of total nitrogen content and protein nitrogen content, is illustrated by the data of Table 15.

The tests were performed on Pinto bean. The plants were treated with solutions of an endogeneous cytokinin (zeatin), synthetic cytokinins and membraneactive regulators according to the invention, respectively, and the leaves of the plants were analyzed 2 weeks after the treatment. The results, compared to the data observed on the controls, are given in Table 15.

to the dry substance content increased by 4–14%, whereas the protein nitrogen content increased by 8–24%. At the same time, the share of protein nitrogen in the total nitrogen content increased from 67% to 70–72%, i.e. an increase of 5–9% could be attained.

Upon the effect of two treatments the total nitrogen content increased by 13–24% and the protein nitrogen content increased by 22–54%. The share of protein nitrogen in the total nitrogen content increased by 5–25%.

The effects of the compositions according to the invention exerted on the crop yield (green yield), crude protein content, protein nitrogen content and C/N ratio of alfalfa, observed under field conditions in the tests performed in 1979 at the Agricultural Combinate of Boly, Hungary, are listed in Table 17.

TABLE 15

| Test No. | Treatment | ppm | Total nitrogen % of dry weight | Total nitrogen Stimulation % | Protein nitrogen % of dry weight | Protein nitrogen Stimulation % | Protein nitrogen content in % of the total nitrogen content |
|---|---|---|---|---|---|---|---|
| 1 | Untreated control | — | 3.8 | — | 2.4 | — | 63 |
| 2 | Zeatin | 20 | 3.8 | — | 2.8 | 16.6 | 73 |
| 3 | kinetin | 30 | 3.8 | — | 2.8 | 16.6 | 73 |
| 4 | Benzyladenine | 30 | 3.8 | — | 2.8 | 16.6 | 73 |
| 5 | 1,4-Dihydroxy-phthalazine di-guanidine salt | 200 | 4.8 | 26.3 | 4.1 | 70.8 | 85 |
| 6 | N—(n-Propyl)-benz-imidazolium bromide | 200 | 5.3 | 39.4 | 4.4 | 83.3 | 83 |

EXAMPLE 26

Stimulation of the total nitrogen content and protein nitrogen content of alfalfa Alfalfa was treated with the compositions according to the invention under large-parcel field conditions. The tests were performed in fourfold replications on parcels 1 hectare in area, each. The oily compositions according to the invention were diluted with water and then sprayed onto the test parcels either once or twice.

The parcels were sprayed first when the soil was already covered with sprouting alfalfa shoots. The second treatment, if any, was performed two weeks later. The dose applied in all of the treatments was 2 kg/ha.

The total nitrogen content and the protein nitrogen content of alfalfa, harvested from the untreated, once-treated and twice-treated parcels, was measured. The results are summarized in Table 16.

TABLE 16

| Test No. | Treatment | Number of treatments | Total nitrogen content % of dry substance | Total nitrogen content Stimulation % | Protein nitrogen content % of dry substance | Protein nitrogen content Stimulation % |
|---|---|---|---|---|---|---|
| 1 | Untreated control | — | 3.36 | — | 2.25 | — |
| 2 | 1,4-dihydroxy-phthalazine diguanidine salt | 1 | 4.17 | 24 | 3.48 | 54 |
| 3 | N—(n-Propyl)-benzimidazolium bromide | 1 | 3.51 | 4 | 2.48 | 8 |
|   |   | 2 | 3.91 | 13 | 2.75 | 22 |

It appears from the test results that, upon a single treatment, the ratio of the total nitrogen content related

TABLE 17

| Test No. | Treatment | Green yield q/ha | Increase % |
|---|---|---|---|
| 1 | Untreated control | 120 | — |
| 2 | 1,4-Dihydroxyphthalazine di-guanidine salt | 146++ | 22.3 |
| 3 | N—Isopropyl-benzimidazolium chloride | 142+ | 18.7 |
| 4 | 2 and 3, applied together | 157++ | 31.4 |

| Test No. | Treatment | Crude protein content (% of dry substance) | Increase % |
|---|---|---|---|
| 5 | Untreated control | 21.3 | — |
| 6 | 1,4-Dihydroxyphthalazine diguanidine salt | 25.4+++ | 19.4 |
| 7 | N—Isopropyl-benzimidazolium chloride | 25.8+++ | 21.5 |
| 8 | 6 and 7, applied together | 27.3++ | 28.6 |

| Test No. | Treatment | $P_2O_5$ content (% of dry substance) | Increase % |
|---|---|---|---|

TABLE 17-continued

| | | | |
|---|---|---|---|
| 9 | Untreated control | 8.3 | — |
| 10 | 1,4-Dihydroxyphthalazine diguanidine salt | 10.3+ | 24.6 |
| 11 | N—Isopropyl-benzimidazolium chloride | 10.9++ | 31.7 |
| 12 | 10 and 11, applied together | 11.4+++ | 38.5 |

| Test No. | Treatment | C/N ratio | Decrease % |
|---|---|---|---|
| 13 | Untreated control | 5.31 | — |
| 14 | 1,4-Dihydroxyphthalazine diguanidine salt | 3.87++ | 27.2 |
| 15 | N—Isopropyl-benzimidazolium chloride | 4.20+ | 21.0 |
| 16 | 14 and 15, applied together | 3.45+++ | 35.1 |

Remarks:
+significance degree: 5%
++significance degree: 1%
+++significance degree: 0.1%

EXAMPLE 27

Stimulating effect exerted on the total nitrogen and protein nitrogen content of mixed soybean/sunflower culture Mixed soybean/sunflower cultures, to be harvested when green, were treated with the compositions according to the invention under large-parcel field conditions. The tests were performed in fourfold replications on parcels 1 hectare in area, each. The compositions were diluted with water and sprayed onto the parcels three times, in doses of 2 kg/ha, each. The first treatment was performed when the soil was already completely covered by green plants, the second treatment was performed two weeks later, and then the third after two additional weeks. The green plants were harvested from the treated and control parcels, and the total nitrogen content and protein nitrogen content were determined. The results are summarized in Table 18.

TABLE 18

| Test No. | Treatment | Total nitrogen content | | Protein nitrogen content | | Protein nitrogen content in % of the total nitrogen content |
|---|---|---|---|---|---|---|
| | | % of dry weight | Stimulation % | % of dry weight | Stimulation % | |
| 1 | Untreated control | 2.56 | — | 2.27 | — | 65.2 |
| 2 | 1,4-Dihydroxyphthalazine diguanidine salt | 3.45 | 34.7 | 3.17 | 39.6 | 94.8 |
| 3 | N—(n-Propyl)-benzimidazolium bromide | 2.80 | 9.7 | 2.75 | 21.1 | 98.9 |

The total nitrogen content increased by 10–35% and the protein nitrogen content by 20–40% upon the effect of the treatments. The share of protein nitrogen content in the total nitrogen content increased by 45–52%, i.e. the most significant increase was attained in this respect. This also involves that the nutrition value of the green plants increased considerably, which is of great importance with respect to animal husbandry.

EXAMPLE 28

Stimulating effect exerted on the green weight, total nitrogen content and protein nitrogen content of maize for silage The tests were performed on parcels 200 m² in area. The compositions according to the invention were utilized as solid formulations, and were diluted with water prior to applying them onto the soil. The active agent was applied to the soil in an amount of 2 kg/ha directly before sowing. The green weight of the maize for silage, harvested from the treated and control parcels, was measured, and the dry substance content, crude protein content, real protein content, nitrogen content and carbon content of the green plants were determined. The results are summarized in Table 19.

TABLE 19

| | | | Treatment with | |
|---|---|---|---|---|
| Test No. | Examined parameter | Untreated control | 1,4-dihydroxyphthalazine diguanidine salt | N—(n-propyl)-benzimidazolium bromide |
| 1 | Green weight, kg | 365 | 374 | 389 |
| 2 | Air-dry substance, absolute % | 20.57 | 22.79++ | 23.48 |
| 3 | Air-dry substance, relative % | — | 10.80 | 14.10 |
| 4 | Crude proteins, absolute % | 1.85 | 2.52+ | 2.25+ |
| 5 | Crude proteins, relative % | — | 36.3 | 21.7 |
| 6 | Real protein content, absolute % | 1.35 | 1.71 | 1.4 |
| 7 | Real protein content, relative % | — | 26.7 | 4.4 |
| 8 | Total carbon content, absolute % | 8.99 | 9.99++ | 10.27++ |
| 9 | Total nitrogen content, absolute % | 0.30 | 0.40+ | 0.86+ |
| 10 | Carbon/nitrogen ratio | 30.86 | 25.27 | 28.67 |

Remarks:
+significance degree: 5%
++significance degree: 1%
+++significance degree: 0.1%

It appears from the data of Table 19 that, upon the effect of the treatment the green weight increased by 2-10%, the dry substance content increased by 10-15%, the crude protein content increased by 20-36%, and the real protein content increased by 4-27%, respectively. As a very favorable result, the carbon/nitrogen ratio decreased by 7-18%.

The effects of the cytokinin-like regulators on the crop yield, crude protein content and real protein content of maize for silage, observed under field conditions in the tests performed in 1979 at the Agricultural Combinate of Boly, Hungary, are listed in Table 20.

TABLE 20

| Test No. | Treatment | Green weight q/ha | Increase % |
|---|---|---|---|
| 1 | Untreated control | 310.2 | — |
| 2 | 1,4-Dihydroxyphthalazine diguanidine salt | 361.3++ | 15.5 |
| 3 | N—Isopropyl-benzimidazolium chloride | 398.2+++ | 28.4 |
| 4 | 2 and 3, applied together | 420.9+++ | 35.7 |

| Test No. | Treatment | Crude protein content (% of dry substance) | Increase % |
|---|---|---|---|
| 5 | Untreated control | 13.2 | — |
| 6 | 1,4-Dihydroxyphthalazine diguanidine salt | 16.0++ | 21.3 |
| 7 | N—Isopropyl-benzimidazolium chloride | 17.1++ | 29.7 |
| 8 | 6 and 7, applied together | 17.9+++ | 35.7 |

| Test No. | Treatment | $P_2O_5$ content (% of dry substance) | Increase % |
|---|---|---|---|
| 9 | Untreated control | 7.5 | — |
| 10 | 1,4-Dihydroxyphthalazine diguanidine salt | 9.5++ | 27.2 |
| 11 | N—Isopropyl-benzimidazolium chloride | 9.8+++ | 30.8 |
| 12 | 10 and 11, applied together | 10.1+++ | 35.6 |

| Test No. | Treatment | C/N ratio | Decrease % |
|---|---|---|---|
| 13 | Untreated control | 31.4 | — |
| 14 | 1,4-Dihydroxyphthalazine diguanidine salt | 25.9++ | 17.6 |
| 15 | N—Isopropyl-benzimidazolium chloride | 23.5+++ | 25.4 |
| 16 | 14 and 15, applied together | 20.4+++ | 35.2 |

Remarks:
+significance degree: 5%
++significance degree: 1%
+++significance degree: 0.1%

EXAMPLE 29

Effect on the grain yield of maize

The compositions according to the invention were applied as seed dressing agents onto the sowing-seeds of hybrid maize in a dosis of 0.5 kg/ha. The powdery compositions were wetted with water prior to application. The stand was sprayed three times during the cultivation period: first at the four-leaves development stage with a dosis of 3 kg/ha, then prior to tasseling with a dosis of 1 kg/ha, and finally prior to pollen ripening with a dosis of 2 kg/ha. The crop was evaluated as May shelled corn. The results are listed in Table 21.

TABLE 21

| Test No. | Treatment | Grain yield q/ha | Increase, % |
|---|---|---|---|
| 1 | Untreated control | 132.8 | — |
| 2 | 1,4-Dihydroxyphthalazine diguanidine salt | 181.9 | 37.0 |

TABLE 21-continued

| Test No. | Treatment | Grain yield q/ha | Increase, % |
|---|---|---|---|
| 3 | N—(n-Propyl)-benzimidazolium bromide | 149.3 | 12.4 |
| 4 | N—Isopropyl-benzimidazolium chloride | 208.5 | 57.1 |
| 5 | A 1:1 mixture of the active agents applied in Tests 2 and 4 | 199.2 | 50.2 |

It appears from the data of Table 21 that the grain yield of maize increased significantly, by 12-57%, upon the treatments performed with the compositions according to the invention.

EXAMPLE 30

Effects on the grain yield of soybean

Soybean cultures were sprayed three times with the compositions according to the invention. The active agents were applied in a dosis of 2 kg/ha, in all of the treatments. The stand was sprayed first at the beginning of flowering, then at the flowering of the apical cluster, and finally two weeks after the second treatment.

The grain yield of soybean, harvested from the treated and control parcels, was measured. The results are listed in Table 22.

TABLE 22

| Test No. | Treatment | Grain yield q/ha | Increase % |
|---|---|---|---|
| 1 | Untreated control | 29.53 | — |
| 2 | 1,4-Dihydroxyphthalazine diguanidine salt | 41.22 | 39 |
| 3 | N—(n-Propyl)-benzimidazolium bromide | 38.67 | 30 |
| 4 | A 1:1 mixture of the active agents applied in Tests 2 and 3 | 39.99 | 35 |

As it appears from the data of Table 22, the grain yield of soybean increased by 30-40% upon the treatments performed with the compositions according to the invention.

EXAMPLE 31

Effects on the grain yield of wheat and on the total and protein nitrogen contents of the grains Two wheat varieties, Libelulla and Mexican 226 K, were utilized in the tests performed under large-parcel field conditions. The sowing seeds were coated with the compositions of the invention according to the wet powder seed dressing technique; a dosis of 2 kg/ha was applied.

The soil was also treated with the compositions according to the invention directly before sowing. A dose of 2 kg/ha was applied.

The grain yields of the wheat varieties, harvested from the treated and control parcels, were measured, and the total nitrogen content and protein nitrogen content of the grains were determined. The results are listed in Tables 23 and 24.

TABLE 23

| | Tests performed on Libelulla wheat variety | | |
|---|---|---|---|
| Test No. | Treatment | Weight of grains collected from 100 ears, g | Increase % |
| 1 | 1,4-Dihydroxyphthalazine diguanidine salt | 232.35 | 7 |
| 2 | N—(n-Propyl)-benzimid- | 357.73 | 65 |

TABLE 23-continued

Tests performed on Libelulla wheat variety

| Test No. | Treatment | Weight of grains collected from 100 ears, g | Increase % |
|---|---|---|---|
| | azolium bromide | | |
| 3 | Untreated control | 215.79 | — |

It appears from the data of Table 23 that the grain yield of Libelulla wheat variety increased somewhat upon treating the plant with a composition containing 1,4-dihydroxyphthalazine diguanidine salt, whereas the composition containing the benzimidazole derivative provoked a significantly greater increase.

TABLE 24

Tests performed on Mexican 226 K wheat variety

| Test No. | Treatment | Total nitrogen content | | Protein nitrogen content | |
|---|---|---|---|---|---|
| | | % of dry substance | Stimulation % | % of dry substance | Stimulation % |
| 1 | 1,4-Hidydroxyphthalazine diguanidine salt | 2.81 | 5.6 | 2.07 | 28.5 |
| 2 | N—(n-Propyl)-benzimidazolium bromide | 2.15 | 1.0 | 1.74 | 8.0 |
| 3 | Untreated control | 2.12 | — | 1.61 | — |

The data of Table 24 indicate that the total nitrogen content of the grains increased somewhat upon the treatment, and the treatment effected a significantly greater increase in protein nitrogen content. In this respect the composition containing the phthalazine derivative proved to be the more active one.

EXAMPLE 32

Effects exerted on the crop yield and sugar content of sugar beet

Glomeruli of sugar beet were treated with the compositions according to the invention (a dose corresponding to 1 kg/ha was applied), and the glomeruli were sown into large parcels. The plants emerged were sprayed twice with the compositions according to the invention, applying a dose of 2 kg/ha, each.

The sugar contents of the plants grown on the treated and control parcels were examined in August. A sugar content of 16.1% was observed with the treated plants, whereas the sugar content of the untreated controls was only 15%.

The crop yield and the sugar content were also determined after harvesting. The results are summarized in Table 25.

TABLE 25

| Test No. | Treatment | Crop yield q/ha | sugar content % | Sugar yield | |
|---|---|---|---|---|---|
| | | | | q/ha | Increase % |
| 1 | Untreated control | 541 | 16.0 | 87.56 | — |
| 2 | 1,4-Dihydroxyphthalazine diguanidine salt | 608 | 16.45 | 100.01 | 14 |
| 3 | N—(n-Propyl)-benzimidazolium bromide | 877 | 17.05 | 149.49 | 70 |

It appears from the data of Table 25 that the sugar yield per hectare increased significantly upon treating the plants with the compositions according to the invention. The composition containing a benzimidazole derivative proved to be particularly effective.

EXAMPLE 33

Effects exerted on the berry yield and sugar content of vine

Vine stands were sprayed with the compositions according to the invention to examine their effects exerted on the berry yield and sugar content. The compositions, diluted with water, were sprayed three times onto the plants. The first treatment was performed prior to flowering, the second one three weeks later, and the third one six weeks after the first one. The dose applied was 2 kg/ha in each of the treatments.

Comparative tests were also performed with commonly used growth regulating compositions, i.e. CCC (chlorocholine chloride), Ethrel (or Etefon; 2-chloroethylphosphonic acid) and Nevirol (N-phenyl-phthalaiminic acid). The results were compared to those observed with the untreated controls.

Two vine varieties, Pannonia and Egri leanyka, were involved in the tests. The results are given in Tables 27 and 28.

TABLE 26

Tests performed on Pannonia vine variety

| Test No. | Treatment | Berry yield q/ha | Sugar content | | Sugar yield | |
|---|---|---|---|---|---|---|
| | | | % | Increase % | q/ha | Increase % |
| 1 | Untreated control | 216 | 13.0 | — | 28.08 | — |
| 2 | 1,4-Dihydroxyphthalazine diguanidine salt | 232 | 20.0 | 53.8 | 46.40 | 62 |
| 3 | N—(n-Propyl)-benzimidazolium bromide | 226 | 15.8 | 21.5 | 35.70 | 27 |
| 4 | CCC | 175 | 16.0 | 23.0 | 28.0 | — |
| 5 | Ethrel | 194 | 14.0 | 7.5 | 27.2 | — |

TABLE 26-continued

Tests performed on Pannonia vine variety

| Test No. | Treatment | Berry yield q/ha | Sugar content % | Increase % | Sugar yield q/ha | Increase % |
|---|---|---|---|---|---|---|
| 6 | Nevirol | 238 | 15.4 | 18.4 | 36.52 | 30 |

TABLE 27

Tests performed on Egri leányka vine variety

| Test No. | Treatment | Berry yield q/ha | Increase % | Sugar content % | Sugar yield q/ha | Increase % |
|---|---|---|---|---|---|---|
| 1 | Untreated control | 151.15 | — | 16.7 | 18.93 | — |
| 2 | 1,4-Dihydroxy-phthalazine di-guanidine salt | 124.23 | — | 16.8 | 15.65 | — |
| 3 | N—(n-Propyl)-benz-imidazolium bromide | 176.92 | 17.0 | 16.7 | 22.16 | 17.0 |
| 4 | CCC | 144.61 | — | 17.0 | 18.44 | — |
| 5 | Ethrel | 164.61 | 8.9 | 15.7 | 19.38 | 2.3 |
| 6 | Nevirol | 169.22 | 11.9 | 16.4 | 20.81 | 9.9 |

The results of the above tests indicate that the compositions exert specific effects on the individual vine varieties. The composition containing a phthalazine derivative of the formula (I) significantly increased the berry yield and sugar content, consequently the sugar yield as well, on Pannonia vine variety, whereas no such effects could be observed on *Egri leányka* vine variety. On the other hand, the composition containing N-(n-propyl)-benzimidazolium bromide effected an increase in crop yield, sugar content and sugar yield on Pannonia vine variety, whereas on *Egri leányka* vine variety it did not influence the sugar content, but increased the crop yield by 17%.

EXAMPLE 34

Effects exerted on the crop yield and protein nitrogen content of grass stand

Tests were performed on grass stands to examine how the compositions according to the invention influence the crop yield, furthermore the total nitrogen content and protein nitrogen content of the crop.

Parcels, 4 m² in area, were separated and pegged out on a grass land, and the parcels were sprayed three times with the compositions according to the invention. The liquid compositions were diluted with water prior to spraying, and spraying was repeated in every two weeks. A dose of 2 kg/ha w was applied in each of the treatments.

Thereafter the grass was mowed, the green crop was weighed, and the total nitrogen content and protein nitrogen content of the mowed grass were determined. The results are listed in Table 28.

TABLE 28

| Test No. | Treatment | Crop yield | Total nitrogen content % | Increase % | Protein nitrogen content % | Increase % |
|---|---|---|---|---|---|---|
| 1 | Untreated control | 5.10 | 4.22 | — | 2.80 | — |
| 2 | 1,4-Dihydroxyphthalazine diguanidine salt | 5.35 | 3.89 | — | 2.62 | — |
| 3 | N—(n-Propyl)-benzimidazolium bromide | 5.27 | 5.36 | 27.0 | 3.54 | 26.4 |

EXAMPLE 35

Increase of the crop yield of edible beans

Edible beans (Superelite variety) were sprayed once or twice with the compositions according to the invention.

The date and number of treatments and the amount of dry beans harvested are listed in Table 29. From the data of Table 29 conclusions can be drawn for the correlation between the development stage of the stand at treatment and the effect of the treatment.

TABLE 29

| Test No. | Treatment | Number of the treatments | Date | Crop yield q/ha | Increase % |
|---|---|---|---|---|---|
| 1 | Untreated control | — | — | 15.00 | — |
| 2 | N—(n-Propyl)-benzimidazolium bromide | 1 | 06.20.1979. | 17.77 | 18.4 |
| 3 | N—(n-Propyl)-benzimidazolium bromide | 1 | 07.06.1979. | 17.03 | 13.5 |
| 4 | N—(n-Propyl)- | 2 | 06.20.1979. | | |

TABLE 29-continued

| Test No. | Treatment | Number of the treatments | Date | Crop yield q/ha | Increase % |
|---|---|---|---|---|---|
|  | benzimidazolium bromide |  | 07.06.1979. | 19.52 | 30.1 |
| 5 | 1,4-Dihydroxy-phthalazine di-guanidine salt | 1 | 07.06.1979. | 17.77 | 18.4 |

EXAMPLE 36

Comparative productive biological evaluation of some benzimidazole derivatives of the general formula (II)

The biological activities of cytokinin-like factors can be well characterized by measuring the intensity of the photosynthetic carbon dioxide fixation and the incorporation of labelled amino acids into the TCA-insoluble protein fraction.

The intensity of photosynthetic carbon dioxide fixation was determined on maize leaves, utilizing $^{14}CO_2$, whereas the incorporation of amino acids was examined on bean leaves, utilizing glycine-2-$^{14}C$. The leaf segments were treated for 18 hours with the solution sof the N-(alkyl)-benzimidazolium bromides, and then exposed for one hour to the effect of the radioactive substances ($^{14}CO_2$ or glycine-2-$^{14}C$). The radioactivities of the treated and control leaf segments are listed in Table 30 in units of $\mu Ci/g$ fresh weight. The standard error of the mean values did not exceed $\pm 7\%$ in each of the measurements.

TABLE 30

| Test No. | Alkyl group | Fixation of $^{14}CO_2$ | | Incorporation of Gly-2-$^{14}C$ | |
|---|---|---|---|---|---|
|  |  | $\mu Ci/g$ | % | $\mu Ci/g$ | % |
| 1 | Untreated control | 5.72 | — | 3.52 | — |
| 2 | Methyl | 8.12 | 42 | 4.75 | 35 |
| 3 | Ethyl | 6.72 | 18 | 4.25 | 21 |
| 4 | Bromoethyl | 6.46 | 13 | 4.36 | 24 |
| 5 | n-Propyl | 10.52 | 84 | 4.96 | 41 |
| 6 | Isopropyl* | 10.92 | 92 | 4.85 | 35 |
| 7 | n-Butyl | 7.49 | 31 | 4.57 | 30 |

*Chloride salt

EXAMPLE 37

Stimulation of carbon dioxide fixation

The method described in Example 21 was applied to determine how the various $R_1$-substituted 1,4-dihydrophthalazine diguanidine salts listed in Table 31 influence the intensity of the photosynthetic carbon dioxide fixation. The tests were performed on Pinto beans, utilizing 200 ppm of active agent, each. The fixation of labelled carbon dioxide ($^{14}CO_2$) was characterized by measuring the radioactivity of the leaf segments. The radioactivities of the leaf segments, expressed in units of dpm/200 mg fresh weight, and the percentage increases are listed in Table 31.

TABLE 31

| Test No. | $R_1$ | Intensity of $CO_2$ fixation | |
|---|---|---|---|
|  |  | dpm | Increase, % |
| 1 | Untreated control | 2.32 | — |
| 2 | Methyl | 3.50 | 50.1 |

TABLE 31-continued

| Test No. | $R_1$ | Intensity of $CO_2$ fixation | |
|---|---|---|---|
|  |  | dpm | Increase, % |
| 3 | Ethyl | 3.58 | 54.3 |
| 4 | Isopropyl | 3.53 | 52.1 |
| 5 | Hydroxyethyl | 3.49 | 50.4 |
| 6 | Chloroethyl | 3.51 | 50.2 |
| 7 | Allyl | 3.50 | 50.1 |
| 8 | Chloro | 3.72 | 60.3 |
| 9 | Bromo | 3.65 | 57.3 |
| 10 | Mercapto | 3.60 | 55.2 |
| 11 | Hydroxy | 3.64 | 56.8 |
| 12 | Methylmercapto | 3.56 | 53.4 |
| 13 | Methoxy | 3.48 | 50.0 |
| 14 | Amino | 3.27 | 40.9 |
| 15 | Methylamino | 3.30 | 42.2 |

EXAMPLE 38

Stimulation of carbon dioxide fixation

The effects of various $R_1$-substituted N-(n-propyl)-benzimidazolium bromides exerted on the photosynthetic fixation of $^{14}CO_2$ were examined as described in Example 37. The results are listed in Table 32.

TABLE 32

| Test No. | $R_1$ | Intensity of $CO_2$ fixation | |
|---|---|---|---|
|  |  | dpm | Increase, % |
| 1 | Untreated control | 2.32 | — |
| 2 | Methyl | 4.26 | 84.0 |
| 3 | Ethyl | 4.13 | 78.0 |
| 4 | n-Propyl | 4.22 | 81.0 |
| 5 | Isopropyl | 4.30 | 85.3 |
| 6 | n-Butyl | 4.20 | 81.0 |
| 7 | Hydroxyethyl | 4.10 | 76.7 |
| 8 | Chloroethyl | 4.00 | 72.4 |
| 9 | Allyl | 4.15 | 78.8 |
| 10 | Chloro | 4.20 | 81.0 |
| 11 | Bromo | 4.10 | 76.7 |
| 12 | Mercapto | 4.32 | 86.2 |
| 13 | Hydroxy | 4.16 | 79.3 |
| 14 | Methylmercapto | 4.00 | 72.4 |
| 15 | Methoxy | 4.09 | 76.2 |
| 16 | Amino | 3.37 | 45.2 |
| 17 | Methylamino | 3.84 | 65.0 |
| 18 | Dimethylamino | 3.76 | 62.0 |

EXAMPLE 39

Effects on the total nitrogen content and protein nitrogen content of soybean

The effects of 1,4-dihydroxyphthalazine and salts thereof exerted on the total nitrogen content and protein nitrogen content of soybean were examined as described in Example 27. The plants were sprayed with the compositions according to the invention at the beginning of the flowering of the apical cluster. The results are listed in Table 33.

TABLE 33

| Test No. | Treatment | Total nitrogen content % of dry substance | Total nitrogen content Increase % | Protein nitrogen content % of dry substance | Protein nitrogen content Increase % |
|---|---|---|---|---|---|
| 1 | Untreated control | 2.6 | — | 1.9 | — |
| 2 | 1,4-Dihydroxyphthalazine | 4.6 | 77.0 | 3.8 | 100.0 |
| 3 | 1,4-Dihydroxyphthalazine diguanidine salt | 4.7 | 81.0 | 3.9 | 105.3 |
| 4 | 1,4-Dihydroxyphthalazine hydrazine salt | 3.7 | 42.4 | 3.1 | 63.2 |
| 5 | 1,4-Dihydroxyphthalazine dihydrazine salt | 3.9 | 50.0 | 3.6 | 89.5 |

The test results listed in Examples 13 to 39 prove that the vegetative and generative biological processes of plants can be influenced effectively with the compositions according to the invention. The treatments result not only in an increase of crop yield, but in most of the cases the quality (composition, nutrient content, nutrient value etc.) of the crop can also be influenced favorably, which represents a significant technical progress.

What we claim is:

1. An agricultural method for increasing the crop yield of a cultivated plant and for improving the quality thereof which comprises the step of treating the cultivated plant, its seeds or its surroundings, with an effective amount of a composition which contains 0.5 to 70% by weight of a mixture of 1,4-dihydroxy-phthalazine-diguanidine and N-(n-propyl)-benzimidazolium bromide together with 30 to 80% by weight of an inert liquid diluent, 1 to 20% by weight of a solid inert carrier, and 1 to 15% by weight of a surfactant.

2. An agricultural method for increasing plant productivity, protein nitrogen level, and anion uptake which comprises the step of applying to a plant an effective amount of a composition which comprises 0.5 to 90% by weight of a mixture of a phthalazine of the formula (I)

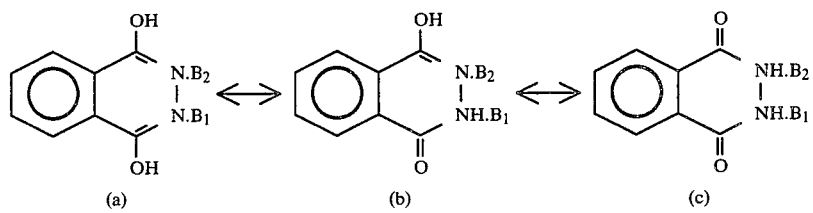

wherein $B_1$ and $B_2$ are each guanidine, and an imidazole of the formula (II)

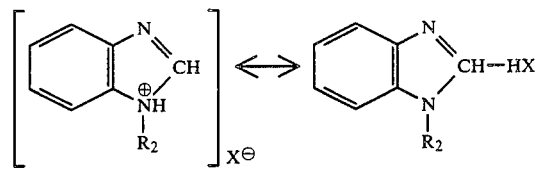

wherein $R_2$ is a straight chain or branched chain $C_1$ to $C_5$ alkyl group, and X is an organic or inorganic anion, wherein the phthalazine and the imidazole are present in a ratio of 4:1 to 1:4 by weight, together with 10 to 95% by weight of an inert solid or liquid carrier, and 1 to 10% by weight of a surfactant.

3. The method defined in claim 2 wherein the composition is applied directly to the cultivated plant prior to sowing or planting.

4. The method defined in claim 2 wherein the composition is sprayed onto the soil after sowing or planting.

5. The method defined in claim 2 wherein the composition is applied to the plant in a dose between 0.5 and 20 kg/ha.

6. The method defined in claim 2 wherein the composition is applied to the plant in a dose between 0.5 and 2 kg/ha.

* * * * *